United States Patent [19]

Ingall et al.

[11] Patent Number: 5,654,285
[45] Date of Patent: Aug. 5, 1997

[54] ADP AND ATP ANALOGUES, PROCESS FOR MAKING AND ADMINISTRATION TO INHIBIT ADP-INDUCED PLATELET AGGREGATION

[75] Inventors: Anthony H. Ingall; Peter A. Cage, both of Leicestershire, England

[73] Assignee: Astra Pharmaceuticals Limited, Hertfordshire, England

[21] Appl. No.: 468,092

[22] Filed: Jun. 6, 1995

Related U.S. Application Data

[63] Continuation of Ser. No. 129,166, filed as PCT/GB92/00590, Apr. 2, 1992, Jan. 19, 1994, abandoned.

[30] Foreign Application Priority Data

Apr. 6, 1991 [GB] United Kingdom ............... 9107236
Nov. 7, 1991 [GB] United Kingdom ............... 9123671

[51] Int. Cl.$^6$ ..................... A61K 31/70; C07H 19/20; C07D 473/00
[52] U.S. Cl. ............... 514/47; 514/48; 514/81; 536/26.23; 536/26.26; 544/264; 544/265
[58] Field of Search ................. 514/45, 46, 47, 514/48, 81; 536/26.23, 26.26; 544/264, 265

[56] References Cited

U.S. PATENT DOCUMENTS 5,049,550  9/1991  Zamecnik ................ 514/47

FOREIGN PATENT DOCUMENTS 9011080  4/1990  WIPO.
9917488  10/1992  WIPO.

OTHER PUBLICATIONS

Cusack et al.(I), "Pharmacological Effects of Isopolar Phosphonate Analogues of ATP on $P_2$–Purinoreceptors in Guinea–Pig Taenia Coli and Urinary Bladder," *Br. J. Pharmac.*, 90(4), 791–795 (1987); *Chem. Abstr.*, 107(1), p. 18, Abstr. No. 258t (1987).

Tseng et al., "Purinergic Receptors in the Brainstem Mediate Hypotension and Bradycardia," *Hypertension*, 11(2), 191–197 (1988); *Chem. Abstr.*, 108(15), p. 124, Abstr. No. 125109x (1988).

McGuire et al., "Specificity of Adenine Nucleotide Receptor Sites: Inhibition of the Guinea Pig Taenia Coli by Adenine Nucleotide Analogs," in *Physiological and Regulatory Functions of Adenosine and Adenine Nucleotides*, Baer and Drummond eds., Raven Press, New York, 1979, pp. 33–43; *Chem. Abstr.*, 92(15), p. 135, Abstr. No. 122601t (1980).

Rabinkov et al., "Interaction of ATP with Acetyl–CoA Carboxylase from Rat Liver. The Role of the Polyphosphate Chain. Affinity Labeling with Alkylating Amides of ATP and ADP," *Biochemie*, 72(10), 719–724 (1990).

Gough et al. (I), "Three New Adenosine Triphosphate Analogs. Synthesis and Effects on Isolated Gut," *J. Med. Chem.*, 16(10), 1188–1190 (1973).

Cusack et al. (II), "Design, Synthesis and Pharmacology of ATP Analogues Selective for Subtypes of $P_2$–Purinoceptors," *Nucleosides and Nucleotides*, 10(5), 1019–1028 (1991).

(List continued on next page.)

Primary Examiner—John Kight
Assistant Examiner—L. Eric Crane
Attorney, Agent, or Firm—Nixon & Vanderhye

[57] ABSTRACT

There are disclosed compounds of formula I,

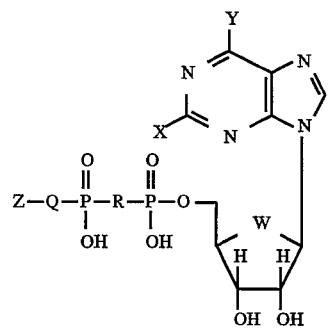

wherein

Q represents $CR^1R^2$,

R represents O or $CR^3R^4$,

W represents O or $CH_2$, $R^1$, $R^2$, $R^3$ and $R^4$ independently represent hydrogen or halogen, X represents $S(O)_nR^5$, alkyl $C_{1-6}$ alkoxy $C_{1-6}$, acylamino $C_{1-6}$, $CONR^6R^7$, $NR^8R^9$, halogen, a 5- or 6-membered S containing heterocycle, or phenyl optionally substituted by alkyl $C_{1-6}$, n represents 0, 1 or 2, $R^5$ represents aryl or alkyl $C_{1-6}$ optionally substituted by one or more substituents selected from hydroxy, alkoxy $C_{1-6}$, halogen and aryl;

$R^6$, $R^7$, $R^8$ and $R^9$ independently represent hydrogen or alkyl $C_{1-6}$, Y represents $NH_2$ or alkoxy $C_{1-6}$, and Z represents an acidic moiety, in addition, when R represents $CR^3R^4$, then —Q—Z may also represent hydroxy or —OP(O)(OH)$_2$, and pharmaceutically acceptable salts thereof, with certain provisos, for use as pharmaceuticals.

11 Claims, No Drawings

OTHER PUBLICATIONS

Blackburn et al.(I), "Synthesis, Physical, Chemical, and Enzyme Studies on Bis-2,6-Diaminopurine β-D-Ribofuranoside $P^1$, $P^4$-Tetraphosphate," *Nucleosides and Nucleotides*, 10(1-3), 549-551 (1991).

Gough et al. (II), "Analogues of Adenosine 5'-Diphosphate—New Platelet Aggregators. Influence of Purine Ring and Phosphate Chain Substitutions on the Platelet Aggregating Potency of Adenosine 5'-Diphosphate," *Molecular Pharmacology*, 8, 170-177 (1972).

Stone et al., "Absence of $P^2$-Purinoceptors in Hippocampal Pathways," *Br. J. Pharmac.*, 97, 631-635 (1989).

Tatham et al., "Characterization of the $ATP^{4-}$ Receptor that Mediates Permeabilisation of Rat Mast Cells," *Eur. J. Pharmac.*, 147(1), 13-21 (1988).

Leff et al., "Quantitative Analysis of the Agonist and Antagonist Actions of Some ATP Analogues at $P_{2x}$-Purinoceptors in the Rabitt Ear Artery," *Br. J. Pharmac.*, 108(2), 490-496 (1993).

Blackburn et al. (II), "Synthesis and Resistance to Enzymatic Hydrolysis of Stereochemically-Defined Phosphonate and Thiophosphate Analogues of $P^1$, $P^4$-Bis(5'-Adenosyl) Tetraphosphate," *Nucleic Acids Res.*, 15(17), 6991-7004 (1987).

Tarussova et al., "The Synthesis of $P^1$, $P^3$ – Bis(5'-Adenosyl) Triphosphate, $P^1$, $P^4$-Bis(5'-Adenosyl Tetraphosphate and Its Phosphonate Analogues with the Use of Carbonyl Derivatives of Nitrogen–Containing Heterocycles," *Bioorganich. Khimya.*, 12(3), 404-407 (1986); see Abstract in English at p. 407.

Guranowski et al., "Phosphonate Analogues of Diadenosine 5', 5'''-$P^1$, $P^4$ Tatraphosphate as Substrates or Inhibitors of Procaryotic and Eucaryotic Enzymes Degrading Dinucleoside Tetraphosphates," *Biochemistry*, 26, 3425-3429 (1987).

Kozarich et al., "Ribonucleoside Phosphate via Phosphoramidazolidate Intermediates. Synthesis of Pseudoadenosine 5'-Triphosphate," *Biochemistry*, 12(22), 4458-4463 (1973).

Blackburn et al. (III), "The Synthesis and Metal Binding Characteristics of Novel, Isopolar Phosphonate Analogues and Nucleotides," *J. Chem. Soc., Perk. Trans. 1*, 1984, 1119-1125.

Cusack et al.(III), "Characterization of ADP Receptors," *Br. J. Pharmacol.*, 87, 84 (1986).

Lüthje et al. (I), "Diadenosine Triphosphate ($Ap_3A$) Mediates Human Platelet Aggregation by Liberation of ADP," *Biochem. Biophys. Res. Comm.*, 118(3), 704-709 (1984).

Lüthje et al (II), "Catabolism of $Ap_3A$ and $Ap_4A$ in Human Plasma," *Eur. J. Biochem.*, 149, 119-127 (1985).

Harrison et al., "Inhibition of Platelet Aggregation and the Platelet Release Reaction by $\alpha, \omega$ Diadenosine Polyphosphates," *FEBS Letters*, 54(1), 57-60 (1975).

Nakajima et al. "Prosthetic Materials Coated with Antithrombogenic Diadenosine Tetraphosphate," *Chem. Abst.*, 110(6), p. 392, Abstr. No. 44985u (1989).

Chao et al., "Inhibition of Platelet Aggregation by $Ap_4A$," *Hoppe-Seyler's Z, Physiol. Chem.*, 365, 610 (1984).

Floodgaard et al., "Ap4A Determination as a Possible Tool for the Diagnosis of Chediak-Higashi Disease and other Platelet Anomalies," *Hoppe-Seyler's Z, Physiol. Chem.*, 365, 610-611 (1984).

Louie et al., "Diadenosine 5',5'''-$p^1,p^4$-tetraphosphate, A Potential Antithrombotic Agent," *Thrombosis Research*, 49, 557-565 (1988).

Hourani et al., "2-MeS-AMP-PCP and Human Platelets: Implications for the Role of Adenylate Cyclase in ADP-induced Aggregation?" *Br. J. Pharmacology*, 87, 84P (1986).

Khorana, Chapter 2 ("Synthesis of Monoesters of Phosphoric Acid") and Chapter 4 (Nucleoside Polyphosphates, Nucleotide Coenzymes, and Related Compounds of Biological Interest: Their Structure and Synthesis) in *Some Recent Developments in the Chemistry of Phosphate Esters of Biological Interest*, John Wiley & Sons, Inc., New York, NY, 1961, pp. 13-43 and 69-92, respectively.

ADP AND ATP ANALOGUES, PROCESS FOR MAKING AND ADMINISTRATION TO INHIBIT ADP-INDUCED PLATELET AGGREGATION

This is a continuation of application Ser. No. 08/129,166, filed as PCT/GB92/00590 2 Apr. 1992, now abandoned.

This invention relates to pharmaceutically useful compounds, and processes for their production.

Adenosine triphosphate (ATP) has potent pharmacological effects on a variety of tissues, the activity of ATP and the other extracellular adenosine nucleotides, adenosine diphosphate (ADP) and adenosine monophosphate (AMP), are mediated by $P_2$-purinoceptors. However, the potency of ATP in some tissues, e.g. the bladder, may be reduced due to rapid dephosphorylation, to AMP and adenosine, by ectonucleotidases present in these tissues.

In recent studies ATP analogues which are resistant to dephosphorylation have been used as biological probes to investigate the $P_2$-purinoceptors present in a variety of tissues:

Cusack et al, *Br. J. Pharmacol.*, 1987, 90, 791–795, describe the activity of 2-methylthio-5'-adenylic acid, monoanhydride with methylenebisphosphonic acid, 2-methylthio-5'-adenylic acid, monoanhydride with dichloromethylenebisphosphonic acid and 2-methylthio-5'-adenylic acid, monoanhydride with difluoromethylenebisphosphonic acid on the guinea pig taenia coli and urinary bladder. Stone and Cusack, *Br. J. Pharmacol.*, 1989, 97, 631–635, describe the use of inter alia 2-methylthio-5'-adenylic acid, monoanhydride with difluoromethylenebisphosphonic acid in an investigation of $P_2$-purinoceptors in the rat hippocampus. Maguire and Satchell in "Physiological and Regulatory Functions of Adenosine and Adenine Nucleotides", Ed. H. P. Baer and G. I. Drummond, Raven Press, New York, 1979, p.33–43, disclose the inhibition of guinea pig taenia coli by the compound 2-chloro-5'-adenylic acid, monoanhydride with methylenebisphosphonic acid.

Cusack and Hourani, *Nucleosides & Nucleotides*, 1991, 10(5), 1019–1028, have also reported that 2-methylthio-5'-adenylic acid, monoanhydride with methylenebisphosphonic acid inhibits ADP-β-S induced platelet aggregation.

We have now found a group of novel 2-substituted ATP derivatives which exhibit pharmacological activity.

According to a first aspect of the present invention, there is provided a compound of formula I,

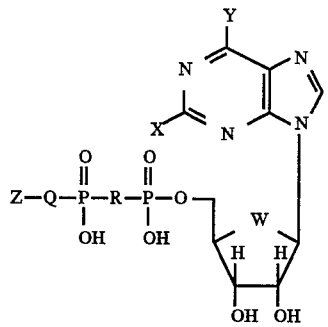

wherein

Q represents $CR^1R^2$,

R represents O or $CR^3R^4$,

W represents O or $CH_2$, $R^1$, $R^2$, $R^3$ and $R^4$ independently represent hydrogen or halogen, X represents $S(O)_nR^5$, alkyl $C_{1-6}$ alkoxy $C_{1-6}$ acylamino $C_{1-6}$, $CONR^6R^7$, $NR^8R^9$, halogen, a 5- or 6-membered S containing heterocycle, or phenyl optionally substituted by alkyl $C_{1-6}$, n represents 0, 1 or 2, $R^5$ represents aryl or alkyl $C_{1-6}$ optionally substituted by one or more substituents selected from hydroxy, alkoxy $C_{1-6}$, halogen and aryl; $R^6$, $R^7$, $R^8$ and $R^9$ independently represent hydrogen or alkyl $C_{1-6}$, Y represents $NH_2$ or alkoxy $C_{1-6}$, and Z represents an acidic moiety, in addition, when R represents $CR^3R^4$, then —Q—Z may also represent hydroxy or —OP(O)(OH)$_2$, provided that:

i) when R is O, W is O, X is Cl, Y is $NH_2$ and Z is —P(O)(OH)$_2$, then $CR^1R^2$ does not represent $CH_2$;

ii) when R is O, W is O, X is $SCH_3$, Y is $NH_2$ and Z is —P(O)(OH)$_2$, then $CR^1R^2$ does not represent (a) $CH_2$, (b) $CF_2$ or (c) $CCl_2$;

iii) when R is $CH_2$, W is O, X is Cl and Y is $NH_2$, then —Q—Z does not represent hydroxy; and iv) when R is O, W is O, X and Y are both $NH_2$ and Z is —P(O)(OH)$_2$, then $CR^1R^2$ does not represent $CH_2$, CHF, $CF_2$, CHCl or $CCl_2$;

and pharmaceutically acceptable salts thereof.

Compounds of formula I may exist in tautomeric, enantiomeric and diastereomeric forms, all of which are included within the scope of the invention.

According to the invention there is further provided a process for the preparation of compounds of formula I, and salts thereof, which comprises:

a) producing a compound of formula I in which R represents O, or a salt thereof, by reacting a compound of formula II, or a salt thereof,

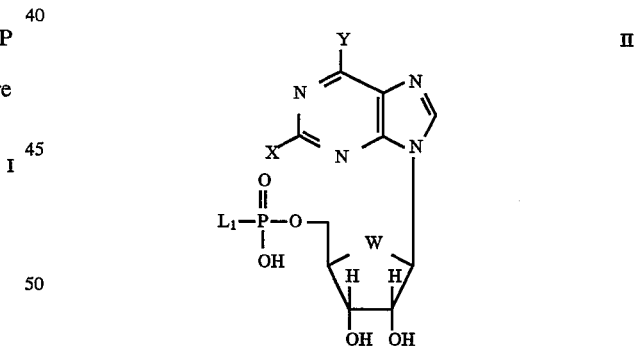

wherein W, X and Y are as defined above and $L_1$ represents a leaving group, with a compound of formula III, or a salt thereof,

wherein Z and Q are as defined above.

b) producing a compound of formula I in which R represents $CR^3R^4$, or a salt thereof, by reacting a compound of formula IV, or a salt thereof,

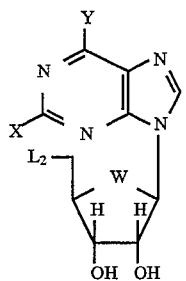

wherein W, X and Y are as defined above and $L_2$ represents a leaving group, with a compound of formula V, or a salt thereof,

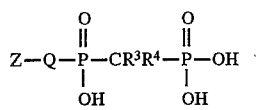

wherein Z, Q, $R^3$ and $R^4$ are as defined above.

c) producing a compound of formula I in which R is $CR^3R^4$ and —Q—Z is —OP(O)(OH)$_2$, or a salt thereof, by reacting a corresponding compound of formula I in which —Q—Z is hydroxy with a compound of formula VI, or a salt thereof,

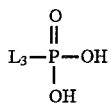

wherein $L_3$ is a leaving group.

d) removal of a protecting group from a corresponding protected compound of formula I in which one or more of the functional groups is protected, and where desired or necessary converting the resultant compound of formula I, or another salt thereof, to a pharmaceutically acceptable salt thereof or vice versa.

In processes a) and c) leaving groups which $L_1$ and $L_3$ may represent include amines, for example, dialkylamines or saturated or unsaturated cyclicamines; particular leaving groups which may be mentioned include morpholinyl, imidazolyl and triazolyl.

In process b) leaving groups which $L_2$ may represent include alkyl or arylsulphonyloxy groups such as methanesulphonyloxy, trifluoromethanesulphonoxy or p-toluenesulphonyloxy; or trifluoroacetoxy.

In processes a), b) and c) the solvent used is preferably a dipolar aprotic solvent, for example, pyridine, dimethylformamide, acetonitrile, hexamethylphosphorictriamide, N,N,-dimethylpropyleneurea or 1-methyl-2-pyrrolidinone. The reaction may be carried out at a temperature of from −20° to 100° C., e.g. from 10° to 30° C.

Compounds of formulae II to VI are either known or may be prepared using methods known to those skilled in the art or by techniques analogous to those given in the examples. For example, compounds of formula II in which $L_1$ represents morpholinyl may be prepared from the corresponding 5'-monophosphates by treatment with morpholine in the presence of a condensing agent such as dicyclohexylcarbodiimide, preferably in the presence of a protic solvent or mixture of solvents such as $t^{butanol}$ and water.

For compounds in which W is O, the nucleoside 5'-monophosphates and nucleosides used in the preparation of the compounds of formulae II and IV respectively are either known or may be prepared from known compounds using known techniques, see, for example, "Chemistry of Nucleosides and Nucleotides" Vol. 2, Ed. Leroy B. Townsend, Plenum Press 1991.

In the above processes it may be necessary for any functional groups, e.g. hydroxy or amino groups, present in the starting materials to be protected, thus process d) may involve the removal of one or more protecting groups.

Suitable protecting groups and methods for their removal are, for example, those described in "Protective Groups in Organic Chemistry" by Theodora Greene, John Wiley and Sons Inc., 1981. Hydroxy groups may, for example, be protected by arylmethyl groups such as phenylmethyl, diphenylmethyl or triphenylmethyl, or as tetrahydropyranyl derivatives. Suitable amino protecting groups include arylmethyl groups such as benzyl, (R,S)-α-phenylethyl, diphenylmethyl or triphenylmethyl, and acyl groups such as acetyl, trichloroacetyl or trifluoroacetyl. Conventional methods of deprotection may be used including hydrogenolysis, acid or base hydrolysis, or photolysis. Arylmethyl groups may, for example, be removed by hydrogenolysis in the presence of a metal catalyst e.g. palladium on charcoal. Tetrahydropyranyl groups may be cleaved by hydrolysis under acidic conditions. Acyl groups may be removed by hydrolysis with a base such as sodium hydroxide or potassium carbonate, or a group such as trichloroacetyl may be removed by reduction with, for example, zinc and acetic acid.

Salts of the compounds of formula I may be formed by reacting the free acid, or a salt thereof, or the free base, or a salt or derivative thereof, with one or more equivalents of the appropriate base or acid. The reaction may be carried out in a solvent or medium in which the salt is insoluble or in a solvent in which the salt is soluble, e.g. ethanol, tetrahydrofuran or diethyl ether, which may be removed in vacuo, or by freeze drying. The reaction may also be a metathetical process or it may be carried out on an ion exchange resin.

Pharmaceutically acceptable salts of the compounds of formula I include alkali metal salts, e.g. sodium and potassium salts; alkaline earth metal salts, e.g. calcium and magnesium salts; salts of the Group III elements, e.g. aluminium salts; and ammonium salts. Salts with suitable organic bases, for example, salts with hydroxylamine; lower alkylamines, e.g. methylamine or ethylamine; with substituted lower alkylamines, e.g. hydroxysubstituted alkylamines; or with monocyclic nitrogen heterocyclic compounds, e.g. piperidine or morpholine; and salts with amino acids, e.g. with arginine, lysine etc, or an N-alkyl derivative thereof; or with an aminosugar, e.g. N-methyl-D-glucamine or glucosamine. The non-toxic physiologically acceptable salts are preferred, although other salts are also useful, e.g. in isolating or purifying the product.

Alkyl groups include straight, branched or cyclic, saturated or unsaturated alkyl groups.

Aryl groups include both carbocyclic and heterocyclic groups. The groups may contain rings of various numbers of C-atoms and may be fused ring structures. Particular carbocyclic aryl groups which may be mentioned are phenyl and naphthyl. Heteroaryl groups include nitrogen, oxygen or sulphur heterocycles and may contain one or more heteroatoms. Examples of heterocycles containing only one heteroatom include pyrrole, furan, thiophen and pyridine. Groups containing more than one heteroatom include pyrazole, oxazole, thiazole, triazole, oxadiazole, thiadiazole etc.

Halogens which X, $R^1$, $R^2$, $R^3$ and $R^4$ may represent include F, Cl, Br and I.

When Q represents $CR^1R^2$, we prefer $R^1$ and $R^2$ to be the same, we particularly prefer compounds in which $R^1$ and $R^2$ both represent Cl.

When R represents $CR^3R^4$, we prefer $R^3$ and $R^4$ to be the same, we particularly prefer compounds in which $R^3$ and $R^4$ both represent hydrogen or Cl.

We prefer compounds in which Q represents $CR^1R^2$.

We prefer compounds in which R represents O.

We particularly prefer compounds of formula I in which Q represents $CR^1R^2$ and R represents O.

We prefer compounds in which W represents O.

S containing heterocycles which X may represent included both saturated and unsaturated heterocycles containing 1 or 2 S atoms. A particular heterocyclic group which may be mentioned is thienyl, particularly 2-thienyl.

We prefer compounds of formula I in which X represents $S(O)_nR^5$, particularly those compounds in which n represents 0. We prefer compounds of formula I in which $R^5$ represents alkyl $C_{1-6}$, particular alkyl groups which may be mentioned include ethyl, butyl and propyl, particularly n-propyl.

We prefer compounds in which Y represents $NH_2$.

Acidic moieties which Z may represent include Bronsted-Lowry acids, i.e. moieties which act as proton donors. The acidic moiety may be mono- or poly-acidic. Specific acidic moieties which may be mentioned include —$P(O)(OH)_2$, —$SO_3H$ and —$CO_2H$.

We prefer compounds of formula I in which Z represents —$P(O)(OH)_2$.

The compounds of formula I are useful because they exhibit pharmacological activity in mammals. In particular, they show activity in the prevention of platelet aggregation.

The potency of the compounds of formula I as inhibitors of platelet aggregation may be determined from their ability to act as $P_{2T}$-receptor antagonists, see Example X.

The compounds may be used in any condition where platelet aggregation or disaggregation is involved. The compounds may thus act as anti-thrombotic agents and are indicated in the treatment or prophylaxis of unstable angina, thromboembolic stroke and peripheral vascular disease. They are also indicated in the treatment or prophylaxis of the sequelae of thrombotic complications from angioplasty, thrombolysis, endarterctomy, coronary and vascular graft surgery, renal dialysis and cardio-pulmonary bypass. Further indications include the treatment or prophylaxis of disseminated intravascular coagulation, deep vein thrombosis, pre-eclampsia/eclampsia, tissue salvage following surgical or accidental trauma, vasculitis, arteritis, thrombocythaemia, ischemia and migraine.

According to a further aspect of the invention, we therefore provide the compounds of formula I, as defined above, but without proviso iv), as pharmaceuticals.

The dosage to be administered will vary widely, depending on, amongst other factors, the particular compound of formula I employed, the particular condition to be treated and its severity. However, in general a total daily dose of 1 g may be suitable, which may be administered in divided doses up to 6 times per day.

The compounds will generally be administered in the form of a pharmaceutical composition.

Thus, according to a further aspect of the invention there is provided a pharmaceutical composition comprising preferably less than 80% w/w, more preferably less than 50% w/w, e.g. 0.1 to 20%, of a compound of formula I, or a pharmaceutically acceptable salt thereof, as defined above, but without proviso iv) in admixture with a pharmaceutically acceptable adjuvant, diluent or carrier.

Examples of pharmaceutical formulations which may be used, and suitable adjuvants, diluents or carriers, are as follows:

for intravenous injection or infusion—purified water or saline solution;

for inhalation compositions—coarse lactose;

for tablets, capsules and dragees—microcrystalline cellulose, calcium phosphate, diatomaceous earth, a sugar such as lactose, dextrose or mannitol, talc, stearic acid, starch, sodium bicarbonate and/or gelatin;

for suppositories—natural or hardened oils or waxes.

When the compound is to be used in aqueous solution, e.g. for infusion, it may be necessary to incorporate other excipients. In particular there may be mentioned chelating or sequestering agents, antioxidants, tonicity adjusting agents, pH-modifying agents and buffering agents.

Solutions containing a compound of formula I may, if desired, be evaporated, e.g. by freeze drying or spray drying, to give a solid composition, which may be reconstituted prior to use.

When not in solution, the compound of formula I preferably is in a form having a mass median diameter of from 0.01 to 10 μm. The compositions may also contain suitable preserving, stabilising and wetting agents, solubilisers, e.g. a water-soluble cellulose polymer such as hydroxypropyl methylcellulose, or a water-soluble glycol such as propylene glycol, sweetening and colouring agents and flavourings. Where appropriate, the compositions may be formulated in sustained release form.

According to a further aspect of the invention we therefore provide the use of a compound of formula I, or a pharmaceutically acceptable salt thereof, but without provisos i), ii)(b), ii)(c), iii) and iv), in the manufacture of a pharmaceutical composition for the treatment of a condition where platelet aggregation or disaggregation is involved.

According to a further aspect of the invention, we therefore provide a method of treating a condition where platelet aggregation or disaggregation is involved which comprises administering a therapeutically effective amount of a compound of formula I, as defined above but without provisos i), ii)(b), ii)(c), iii) and iv) to a patient suffering from such a condition.

The compounds of the invention are advantageous in that they are less toxic, more efficacious, are longer acting, have a broader range of activity, are more potent, are more stable, produce fewer side effects, are more easily absorbed, are more readily cleared from the body or have other useful pharmacological properties, than compounds previously used in the therapeutic fields mentioned above.

The invention is illustrated, but in no way limited, by the following Examples, in which temperatures are given in degrees Celsius. Examples are named using Chemical Abstracts nomenclature.

EXAMPLE 1

2-Propylthio-5'-adenylic acid, monoanhydride with dibromomethylenebisphosphonic acid, tetrasodium salt i) 2-Propylthioadenosine Adenosine-2-thione (2.5 g) in water (15 ml), methanol (45 ml) and 1N sodium hydroxide solution (8.36 ml) were cooled in an icebath and iodopropane (5 ml) introduced. After 4 days the reaction mixture was evaporated and the residue chromatographed ($SiO_2$, ethyl acetate:methanol, 9:1) to afford the sub-title compound in quantitative yield.

NMR $\delta^1H$ ($d^6DMSO$) 8.22 (s, 1H), 7.36 (brs, 2H), 5.80 (d, 1H, J=5.9 Hz), 5.61 (t, 1H, J=5.5 Hz), 5.13 (m, 1H), 3.90 (dd, 1H, J=4.0 and 7.7 Hz), 3.64 (dd, 1H, J=4.2 and 11.8 Hz), 3.52 (dd, 1H, J=4.4 and 11.8 Hz), 3.0–3.2 (m, 2H), 1.67 (hextet, 2H, J=7.3 Hz), 0.99 (t, 3H, J=7.3 Hz).

ii) 2-Propylthio-5'-adenylic acid

The product of step i) (1.0 g) was added to a stirred mixture of phosphorus oxychloride (1.06 ml) and triethyl phosphate (25 ml) at −10° C. After 3 hours the reaction mixture was poured onto ice and the pH adjusted to 7 with solid sodium bicarbonate. The solution was washed with ether (3×150 ml) and then lyophilised. The resulting solid was taken in deionised water and applied to a column of Dowex 50W×8 (H⁺ form), which was washed with water until the eluate was at pH 6, then eluted with 1M ammonium hydroxide. Lyophilisation afforded the sub-title compound (0.4 g).

NMR $\delta^{31}$P (D$_2$O) 1.32 (s).

iii) 2-Propylthio-5'-adenylic acid, monoanhydride with dibromomethylenebisphosphonic acid, tetrasodium salt The product of step ii) (0.4 g) and tri-n-butylamine (0.175 g) were combined in a small volume of water and the solution evaporated to dryness. Azeotropic drying with pyridine (3×15 ml) followed by anhydrous dimethylformamide (2×15 ml) left a residue which was taken into anhydrous dimethylformamide (10 ml). Carbonyldiimidazole (0.77 g) was added, and the reaction left at room temperature for 4 hours before adding methanol (0.24 g). After 30 min the mono tri-n-butylammonium salt of dibromomethylenebisphosphonic acid (6.5 mmol) in anhydrous dimethylformamide (30 ml) was added, and the mixture stirred at room temperature for 18 hours. Filtration and evaporation afforded a residue which was purified by chromatography (DEAE-Sepharose, aqueous ammonium bicarbonate 0–0.4M as eluant). Lyophilisation gave the ammonium salt which was redissolved in water (200 ml) and treated with triethylamine (10 ml). Evaporation in vacuo produced the tetrakistriethylammonium salt which was converted to the tetrasodium form by dissolution in methanol (2 ml) and addition of sodium iodide solution (1M in acetone, 30 ml). The precipitate was collected by centrifugation, washing by repeated suspension in acetone (4×40 ml) and recentrifugation. Finally the solid was dissolved in water and lyophilised to afford the title salt as a white powder (0.42 g).

NMR $\delta^{31}$P (D$_2$O) 8.95 (d, J=36 Hz), 1.35 (dd, J=36 and 69 Hz), −9.15 (d, J=69 Hz).

EXAMPLE 2

The following compounds were prepared according to the method of Example 1:

a) 2-Propylthio-5'-adenylic acid, monoanhydride with difluoromethylenebisphosphonic acid, tetrasodium salt NMR $\delta^{31}$P (D$_2$O) 3.94 (dt, J=145.8 and 196 Hz), 3.11 to −4.92 (m), −10.15 (d, J=75 Hz).

b) 2-Propylthio-5'-adenylic acid, monoanhydride with dichloromethylenebisphosphonic acid, tetrasodium salt NMR $\delta^{31}$P (D$_2$O) 9.4 (d, J=46 Hz), 2.3 (dd, J=46 and 73.1 Hz), −9.15 (d, J=73.1 Hz).

c) 2-Pentylthio-5'-adenylic acid, monoanhydride with dichloromethylenebisphosphonic acid, tetrasodium salt i) 2-Pentylthioadenosine NMR $\delta^1$H (d$_6$DMSO) 8.22 (s, 1H), 7.35 (brs, 1H), 5.80 (d, 1H, J=5.9 Hz), 5.42 (d, 1H, J=6.16 Hz), 5.16 (d, 1H, J=4.86 Hz), 5.02 (t, 1H, J=5.6 Hz), 4.61 (q, 1H, J=5.76 Hz), 4.07–4.15 (m, 1H), 3.85–3.95 (m, 1H), 3.6–3.7 (m, 1H), 3.48–3.6 (m, 1H), 3.0–3.15 (m, 2H), 1.6–1.7 (m, 2H), 1.3–1.45 (m, 4H), 0.88 (t, 3H, J=7.02 Hz).

ii) 2-Pentylthio-5'-adenylic acid

NMR $\delta^{31}$P (D$_2$O) 1.2 (s).

iii) 2-Pentylthio-5'-adenylic acid, monoanhydride with dichloromethylenebisphosphonic acid, tetrasodium salt NMR $\delta^{31}$P (D$_2$O) 8.55 (d, J=46.2 Hz), 2.5–3.5 (m), −9.12 (d, J=70.34 Hz).

d) 2-Pentylthio-5'-adenylic acid, monoanhydride with dibromomethlenebisphosphonic acid, monoammonium salt Purification of the crude product by chromatography (DEAE-Sepharose, ammonium bicarbonate 0–0.4M as eluant) afforded the title salt.

NMR $\delta^{31}$P (D$_2$O) 7–8 (brs), 2.5–3.5 (m), −9.07 (d, J=83.5 Hz).

e) 2-Ethylthio-5'-adenylic acid, monoanhydride with dichloromethylenebisphosphonic acid, tetrasodium salt i) 2-Ethylthio-5'-adenylic acid, disodium salt NMR $\delta^{31}$P (D$_2$O) 5.01 (s).

ii) 2-Ethylthio-5'-adenylic acid, monoanhydride with dichloromethylenebisphosphonic acid, tetrasodium salt NMR $\delta^{31}$P (D$_2$O) 8.25 (d, J=17.04 Hz), 3.28 (dd, J=18.9 and 28.22 Hz), −9.22 (d, J=28.22 Hz).

f) 2-Ethylthio-5'-adenylic acid, monoanhydride with dibromomethylenebisphosphonic acid, tetrasodium salt NMR $\delta^{31}$P (D$_2$O) 6.5–7.5 (m), 2.88 (dd, J=14.75 and 27.33 Hz), −10.9 (d, J=28.22 Hz).

g) 2-Butylthio-5'-adenylic acid, monoanhydride with dichloromethylenebisphosphonic acid, monoammonium salt i) 2-Butylthio-5'-adenylic acid NMR $\delta^{31}$P (D$_2$O) 1.84 (s).

ii) 2-Butylthio-5'-adenylic acid, monoanhydride with dichloromethylenebisphosphonic acid, monoammonium salt NMR $\delta^{31}$P (D$_2$O) 8.05–8.25 (m), 3.66 (dd, J=18.48 and 27.8 Hz), −9.03 (d,. J=27.8 Hz).

h) 2-Propylthio-5'-adenylic acid, monoanhydride with methylenebisphosphonic acid, tetrasodium salt NMR $\delta^{31}$P (D$_2$O) 15.8 (d, J=8.3 Hz), 10.7 (dd, J=8.4 and 27 Hz), −9.44 (d, J=25.8 Hz).

i) 2-Acetamido-5'-adenylic acid, monoanhydride with dibromomethylenebisphosphonic acid, tetrasodium salt i) 2-Acetamido-5'-adenylic acid NMR $\delta^{31}$P (D$_2$O) 4.16 (s).

ii) 2-Acetamido-5'-adenylic acid, monoanhydride with dibromomethylenebisphosphonic acid, tetrasodium salt NMR $\delta^{31}$P (D$_2$O) 8.99 (d, J=14.7 Hz), 1.42 (dd, J=14.8 and 28.3 Hz), −9.16 (d, 28.3 Hz).

j) 2-Chloro-5'-adenylic acid, monoanhydride with dichloromethylenebisphosphonic acid, tetrasodium salt UV $\lambda_{max}$ (H$_2$O) 210 nm ($\epsilon$ 20,900), 265 nm ($\epsilon$ 12,700).

k) 2-Iodo-5'-adenylic acid, monoanhydride with difluoromethylenebisphosphonic acid, tetrasodium salt NMR $\delta^{31}$P (D$_2$O) 4.72 (dt, J=57 and 73 Hz), −1.89 (ddt, J=64, 88 and 31 Hz), −9.86 (d, J=32 Hz).

l) L-2-Methylthio-5'-adenylic acid, monoanhydride with dibromomethylenebisphosphonic acid, tetrasodium salt NMR $\delta^{31}$P (D$_2$O) 8.12 (d, J=15 Hz), −0.03 (dd, J=15 and 26 Hz), −9.88 (d, J=28 Hz).

m) 2-Propylamino-5'-adenylic acid, monoanhydride with dichloromethylenebisphosphonic acid, trisodium salt NMR $\delta^{31}$P (D$_2$O) 8.87 (d), 0.99 (dd), −9.3 (d).

n) 2-Propylthio-5'-adenylic acid, monoanhydride with sulphodifluoromethylphosphonic acid, trisodium salt NMR $\delta^{31}$P (D$_2$O) −8.8 (dt), −10.0 (d).

o) 2-Propylthio-5'-adenylic acid, monoanhydride with phosphonoacetic acid, trisodium salt NMR $\delta^{31}$P (D$_2$O) 11.4 (d), −9.57 (d).

p) 2-(2-Thienyl)-5'-adenylic acid, monoanhydride with dibromomethylenebisphosphonic acid, tetrasodium salt i) 2-(2-Thienyl)-5'-adenylic acid NMR $\delta^{31}$P (D$_2$O) 2.14 (s).

ii) 2-(2-Thienyl)-5'-adenylic acid, monoanhydride with dibromomethlenebisphosphonic acid, tetrasodium salt NMR $\delta^{31}$P (D$_2$O) 9.53 (d, J=14 Hz), 3.91 (dd, J=14 and 30 Hz), −8.96 (d, J=30 Hz).

q) 2-Phenyl-5'-adenylic acid, monoanhydride with dibromomethylenebisphosphonic acid, tetrasodium salt i) 2-Phenyl-5'-adenylic acid NMR $\delta^{31}$P (D$_2$O) 0.22 (s).

ii) 2-Phenyl-5'-adenylic acid, monoanhydride with dibromomethylenebisphosphonic acid, tetrasodium salt NMR $\delta^{31}$P (D$_2$O) 8.55 (d, J=14.1 Hz), 2.92 (dd, J=14.2 and 29.6 Hz), –9.87 (d, J=29.8 Hz).

EXAMPLE 3

2-Butyl-5'-adenylic acid, monoanhydride with dibromomethylenebisphosphonic acid, trisodium salt.

i) 2-Butyl-5'-adenylic acid

The product of Example 2p)i) (1.4 g) was heated with activated Raney nickel (1.5 g) in water (50 ml) at 70° C. for 2 hours. After filtration and washing of the solid with water, evaporation of the filtrate afforded the sub-title compound as a colourless solid (0.56 g).

MS (FAB) 404 (M$^+$+1), 426 (M$^+$+Na), 192 (100%).

ii) 2-Butyl-5'-adenylic acid, monoanhydride with dibromomethylenebisphosphonic acid, trisodium salt.

NMR $\delta^{31}$P (D$_2$O) 8.8 (d) , 1.0 (dd), –9.4 (d).

EXAMPLE 4

2-Propoxy-5'-adenylic acid, monoanhydride with dibromomethylenebisphosphonic acid, tetrasodium salt i) 2-Propoxy-adenosine 2-Chloro-adenosine (3.5 g) was added to a hot solution of NaOH (3.2 g) in n-propanol (80 ml), the mixture was heated under reflux for 3 hours. The volatiles were removed in vacuo, the residue taken into water (40 ml), cooled and acidified with 1M hydrochloric acid to pH 7. After 15 min the suspension was filtered and the filtrate evaporated. The residue was taken up in ethanol, and adsorbed onto silica which was placed on a chromatography column. Elution with 9:1, and then 4:1 CHCl$_3$ afforded the sub-title compound (0.65 g).

MS (FAB) 326 (M$^+$+H).

ii) 2-Propoxy-5'-adenylic acid, monoammonium salt

Prepared by the method of Example 1.

NMR $\delta^{31}$P (D$_2$O+NaOD) 3.17 (s).

iii) 2-Propoxy-5'-adenylic acid, monoanhydride with dibromomethylenebisphosphonic acid, tetrasodium salt NMR $\delta^{31}$P (D$_2$O) 9.4 (d, J=14.5 Hz), 3.77 (dd, J=14.3 and 29.2 Hz), –9.0 (d, J=29.7 Hz).

EXAMPLE 5

2-(1-Methylethyl)thio-5'-adenylic acid, monoanhydride with dichloromethylenebisphosphonic acid, trisodium salt i) 2',3',5'-Tri-O-acetyl-6-chloro-2-(1-methylethyl)thio-adenosine 9-(2',3',5'-Tri-O-acetyl-β-D-ribofuranosyl)-2-amino-6-chloropurine (6.6 g) was dissolved in dry acetonitrile (65 ml). Isopropyl disulphide (21 ml) and isoamyl nitrite (12.1 ml) were added and the resulting solution purged with nitrogen for 45 min, then heated under nitrogen at 60° for 16 hours. The volatiles were removed in vacuo and the residue chromatographed to afford the sub-title compound as a yellow oil (3.69 g).

NMR $\delta^1$H (d$_6$-DMSO) 8.70 (s, 1H), 6.29 (d, 1H), 6.02 (m, 1H), 5.61 (t, 1H), 4.39 (m, 2H), 4.20 (m, 1H), 4.00 (septet, 1H), 2.12, 2.07, 1.98 (3×s, 3×1H), 1.41 d, 6H).

ii) 2-(1-Methylethyl)thio-adenosine

The product of step i) (3.6 g) in ethanol (400 ml) was cooled to 0° and saturated with ammonia. The solution was allowed to warm to approx. 15°, then heated to 70° in an autoclave for 24 hours, the volatiles were removed in vacuo and the residue chromatographed to afford the sub-title compound (1.95 g).

MS (FAB) 342 (M$^+$+H) (100%).

iii) 2-(1-Methylethyl)thio-5'-adenylic acid

The sub-title compound was prepared according to the method of Example 1.

NMR $\delta^{31}$P (D$_2$O) 1.1 (s).

iv) 2-(1-Methylethyl)thio-5'-adenylic acid, monoanhydride with dichloromethylenebisphosphonic acid, trisodium salt The title compound was prepared according to the method of Example 1.

NMR $\delta^{31}$P (D$_2$O) 9.21 (d, J=21 Hz), 2.0 (dd, J=19 and 30 Hz), –9.33 (d, J=32 Hz).

EXAMPLE 6

2-Propylthioadenosine, 5'-P$^1$ monoester with bis[(dihydroxyphosphinyl]methyl]phosphinic acid, disodium salt i) 2',3'-O,O-(1-Methylethylidene)-2-propylthioadenosine To a suspension of 2-propylthioadenosine (2.6 g) in AR acetone (97 ml) and 2,2-dimethoxypropane (11.3 ml) was added p-toluenesulphonic acid monohydrate (1.46 g) in small portions over 1 hour. The resulting solution was stirred at ambient temperature for 18 hours, diluted with water (300 ml) and treated with triethylamine to pH 7. The volume was reduced to half in vacuo, and the remaining solution extracted into chloroform (3×100 ml). The extract was dried (MgSO$_4$), filtered and evaporated. The residue was purified by chromatography (SiO$_2$, ethyl acetate) to afford the sub-title compound (1.8 g).

MS (FAB) 382 (M$^+$+H), BP 210.

ii) 5'-4-Methylbenzenesulphonyl-2',3'-O,O-(1-methylethylidene)-5'-deoxy-2-propylthioadenosine To an ice-cooled solution of the product of step i) (1.6 g) in dry dichloromethane (100 ml) was added 4-dimethylaminopyridine (1.33 g) and then a solution of p-toluenesulphonyl chloride (0.88 g) in dry dichloromethane (20 ml) over 15 min. After 18 hours at 0°–4° the volatiles were removed in vacuo and the residue purified by chromatography (SiO$_2$, ethyl acetate) to afford the sub-title compound (1.9 g).

NMR $\delta^1$H (CDCl$_3$) 7.7 (s, 1H), 7.6 (d, 2H), 7.1 (d, 2H), 6.0 (d, 1H), 5.7 (s, 2H), 5.4 (d, 1H), 5.0 (m, 1H), 4.4 (m, 1H), 4.2 (m, 2H), 3.0 (m, 2H), 2.4 (s, 3H), 1.7 (q, 2H), 1.6 (s, 3H), 1.4 (s, 3H), 1.1 (t, 3H).

iii) 2-Propylthioadenosine, 5'-P$^1$ monoester with bis-[(dihydroxyphosphinyl)methyl]phosphinic acid, disodium salt A solution of bis[(dihydroxyphosphinyl)methyl]phosphinic acid (0.66 g) in water (10 ml) was adjusted to pH 8.7 by addition of 40% w/v tetrabutylammonium hydroxide solution, then lyophilised to afford a gum, which was further dried by repeated dissolution in acetonitrile and evaporation of the solvent (3×50 ml). The residue was taken in dry acetonitrile (10 ml) and treated with the product of step ii) (0.81 g) and the mixture concentrated in vacuo to a thick syrup. After stirring overnight at ambient temperature the mixture was diluted with water and applied to a column of DEAE-Sepharose (Fast Flow). Elution with 0–0.6M triethylammonium afforded, after lyophilisation, a residue which was dissolved in 80% v/v acetic acid and heated to 80° for 4 hours. After evaporation to dryness the residue was azeotroped with water (2×20 ml), dissolved in methanol (5 ml) and treated with a few drops of triethylamine. To this solution was added 1M sodium iodide in acetone to precipitate the sodium salt, which was collected by centrifugation, and washed several times with acetone. The solid was taken up in water and freeze-dried to yield the title salt as a colourless solid (96 mg).

NMR $\delta^{31}P$ ($D_2O$) 28.17 (d), 18.86 (dd), 16.39 (d).

EXAMPLE 7

2-Propylthioadenosine, 5'-$P^1$ monoester with bis[(dichloro(dihydroxyphosphinyl))methyl]phosphinic acid, tetrasodium salt i) bis[(dichloro(dihydroxyphosphinyl))methyl]phosphinic acid, pentaethyl ester A solution of bis[(dihydroxyphosphinyl)methyl]phosphinic acid pentaethyl ester (3.94 g) in chloroform (100 ml) was vigorously stirred with commercial sodium hypochlorite solution (5.25% available chlorine, 400 ml) at ambient temperature for 24 hours. The organic phase was separated and evaporated to afford the sub-title compound (4.7 g).

MS (FAB) 531/533/535/537 ($M^+$+H), BP 533.

ii) bis[(dichloro(dihydroxyphosphinyl))methyl]phosphinic acid

The product of step i) (0.532 g) in dry methylene chloride (10 ml) was treated with trimethylsilyl bromide (0.912 g) at ambient temperature for 18 hours. The volatiles were removed in vacuo, and the residue taken up in methanol (5 ml) which was evaporated after 2 hours, the resulting oil was taken up in deionised water (10 ml) and extracted well with ether. Cyclohexylamine was added until the pH was approx. 10, then methanol was added until a turbidity persisted. The solid which deposited on cooling was collected and dried, then taken up in water (10 ml) and applied to a Dowex 50W×8 ($H^+$) column. Elution with distilled water and lyophilisation afforded the sub-title compound (0.15 g).

NMR $\delta^{31}P$ ($D_2O$) 9.2 (d, J=20.4 Hz), 17.9 (t, J=18.7 Hz).

iii) 2-Propylthioadenosine, 5'-$P^1$ monoester with bis[(dichloro(dihydroxyphosphinyl))methyl]phosphinic acid, tetrasodium salt The title compound was prepared from the product of step ii) according to the method of Example 6 (0.35 g).

NMR $\delta^{31}P$ ($D_2O$) 20.81 (t, J=14.1 Hz), 11.18 (d, J=12.1 Hz), 9.9 (d, J=12.3 Hz).

EXAMPLE 8

2-Propylthioadenosine, 5'-$P^1$ monoester with methylenebisphosphonic acid, $P^2$-monoanhydride with phosphoric acid, tetrasodium salt i) 2-Propylthioadenosine, 5'-$P^1$ monoester with methylenebisphosphonic acid, disodium salt The sub-title compound was prepared by the method of Example 6iii).

NMR $\delta^{31}P$ ($D_2O$) 20.97 (d, J=8.56 Hz), 15.3 (d, J=8.57 Hz).

ii) 2-Propylthioadenosine, 5'-$P^1$ monoester with methylenebisphosphonic acid, $P^2$-monoanhydride with 1-(2-nitrophenyl)ethyl phosphate, monotriethyl- ammonium salt The product of step i) was eluted through a column of Dowex 50W×8 (n-$Bu_4^{N+}$ form) with deionised water and the effluent was lyophilised to afford the tetra-n-butylammonium salt of the bisphosphonate material. This salt (0.73 mmol) and 1-(2-nitrophenyl)ethyl phosphoromorpholidate, N,N'-dicyclohexyl morpholine-1-carboxamidinium salt (1.09 mmol) were stirred in dry pyridine (5 ml) for 48 hours at ambient temperature. The solvent was evaporated and the residue taken up in water (100 ml) and washed with chloroform (2×50 ml). The volume of the aqueous phase was reduced to 10 ml at 30° and applied to a column of DEAE-Sepharose which was eluted with 0–0.4M triethylammonium bicarbonate solution. The appropriate fractions were combined and lyophilised to afford the sub-title compound (0.3 g).

NMR $\delta^{31}P$ ($D_2O$) 18.43 (d, J=11.31 Hz), 7.8 (dd), −10.96 (d, J=26.3 Hz).

iii) 2-Propylthioadenosine, 5'-$P^1$ monoester with methylenebisphosphonic acid, $P^2$-monoanhydride with phosphoric acid, tetrasodium salt The product of step ii) (0.3 g) in 0.4M triethylammonium bicarbonate solution (100 ml) containing semicarbazide hydrochloride (0.3 g) at 10° was irradiated with a high pressure UV lamp for 2 hours. The solvent was removed in vacuo at 30° and the residue purified by chromatography on DEAE-Sepharose eluted with 0–0.6M triethylammonium bicarbonate buffer. The relevant fractions were combined and lyophilised and the residue converted to the tetrasodium salt by the method of Example 6iii) (1.13 g).

NMR $\delta^{31}P$ ($D_2O$) 19.34 (d, J=8.56 Hz), 6.7 (dd), −6.6 (d, J=20.96 Hz).

EXAMPLE 9

3-(6-Amino-2-propylthio-9H-purin-9-yl)-5-(hydroxymethyl)-1,2-cyclopentanediol 5-dihydrogen phosphate, monoanhydride with dichloromethylenebisphosphonic acid, trisodium salt i) 2-Propylthio-pyrimidine-4,6-diol To a solution of 4,6-dihydroxy-2-mercaptopyrimidine (100 g) in potassium hydroxide (2.5N, 571 ml) was added propyl iodide (76.8 ml) and the whole was stirred for 4 days. The solution was acidified to pH 2–3 and filtered to afford the sub-title compound (15 g).

MS 330 $M^+$ (di-TMS), BP 315.

ii) 5-Nitro-2-propylthiopyrimidine-4,6-diol

The product of step i) (2 g) was added to ice-cooled fuming nitric acid (10 ml) over 1 hour and stirred at 0° for a further 1 hour. Pouring into ice followed by drying afforded the sub-title compound as a beige solid (1.7 g).

MS 375 $M^+$ (di-TMS), BP 360.

iii) 4,6-Dichloro-5-nitro-2-propylthiopyrimidine The product of step ii) (1.7 g), phosphoryl chloride (10 ml) and N,N-diethylaniline (3 ml) were heated to reflux for 1 hour, then concentrated to half volume and poured onto ice to yield a black tar. Extraction of the tar with ether afforded a solution which was dried ($MgSO_4$) then evaporated. The residue was chromatographed ($SiO_2$, light petrol) to afford the sub-title compound (0.8 g).

MS 267/269/271 $M^+$, BP 41.

iv) 4,6-Dichloro-2-propylthio-pyrimidine-5-amine

To a solution of the product of step iii) (1 g) in glacial acetic acid (10 ml) was added reduced iron powder (1.1 g). The temperature was reduced to 60° by cooling and then heated at 60° for 15 min. The reaction was evaporated to dryness and the residue extracted into ether (100 ml), washed with dilute sodium hydroxide solution and dried. Evaporation afforded the sub-title compound as a dark oil (0.8 g).

NMR δ¹H (CDCl₃) 4.2 (brs, 2H), 3.1 (t, 2H), 1.71 (q, 2H), 1.05 (t, 3H).

v) 3-(5-Amino-6-chloro-2-propylthiopyrimidine-4-ylamino)-5-(hydroxymethyl)-cyclopentane-1,2-diol The product of step iv) (4.6 g) was added to a solution of 3-amino-5-(hydroxymethyl)-cyclopentane-1,2-diol (1.41 g) in butan-1-ol (200 ml) containing triethylamine (10 ml) and the whole heated to reflux for 48 hours. Evaporation gave a dark residue which was chromatographed (SiO₂, 10% ethanol/dichloromethane) to afford the sub-title compound (2.8 g).

MS 349/350 (M⁺+H), BP 349.

vi) 3-(6-Amino-2-propylthio-9H-purin-9-yl)-5-(hydroxymethyl)-1,2-cyclopentanediol The product of step v) (0.2 g) and diethoxymethyl acetate (10 ml) were stirred at ambient temperature under nitrogen for 1 hour, then at 80° for 24 hours. Evaporation afforded a residue which was treated with liquid ammonia (15 ml) in an autoclave at 60° for 16 hours. The ammonia was allowed to evaporate and the residue taken up in 0.5M hydrochloric acid (10 ml) at 60° for 45 min. The volatiles were removed in vacuo and the remaining material dissolved in water (10 ml). Upon neutralisation with concentrated ammonia the sub-title compound crystallised and was collected and dried (0.15 g).

MS (FAB) 340 (M⁺+H), BP 340.

vii) 3-(6-Amino-2-propylthio-9H-purin-9-yl)-5-(hydroxymethyl)-1,2-cyclopentanediol 5-dihydrogen phosphate The product of step vi) was converted to the sub-title compound by the method of Example 1.

NMR δ³¹P (D₂O) 2.85 (s).

viii) 3-(6-Amino-2-propylthio-9H-purin-9-yl)-5-(hydroxymethyl)-1,2-cyclopentanediol 5-dihydrogen phosphate, monoanhydride with dichloromethylenebisphosphonic acid, trisodium salt The product of step vii) was converted to the title salt by the method of Example 1.

NMR δ³¹P (D₂O) 8.54 (d, J=18.73 Hz), 0.84 (dd), −9.5 (d, J=29.61 Hz).

EXAMPLE 10

1-(6-Methoxy-2-propylthio-purin-9-yl)-ribofuranos-5'-yl-phosphate, monoanhydride with dichloromethylenebisphosphonic acid, trisodium salt i) 2',3',5'-Tri-O-acetyl-6-chloro-2-propylthioadenosine The sub-title compound was prepared according to the method of Example 5i), using Di-n-propyl disulphide.

NMR δ¹H (CDCl₃) 8.13 (s, 1H), 6.14 (d, 1H), 5.93 (t, 1H), 5.60 (t, 1H), 4.3–4.5 (m, 3H), 3.21 (t, 2H), 2.15, 2.13, 2.11 (3×s, 3×3H), 1.8 (m, 2H), 1.07 (t, 3H).

ii) 6-Methoxy-2-propylthio-9-ribofuranosyl-purine

The compound from step i) (5.2 g) was dissolved in 1M sodium methoxide in methanol solution (53 ml) and heated to reflux for 1 hour under nitrogen. Dilution with water (100 ml), neutralisation with dilute hydrochloric acid and evaporation of the methanol gave an oil. Trituration with water and then dichloromethane afforded the sub-title compound as a colourless solid (1.35 g).

MS (FAB) 357 (M++H), BP 225.

iii) 1-(6-Methoxy-2-propylthio-purin-9-yl)-ribofuranos-5'-yl-phosphate

The sub-title compound was prepared according to the method of Example 1.

NMR δ³¹P (D₂O) 1.69 (s). iv) 1-(6-Methoxy-2-propylthio-purin-9-yl)-ribofuranos-5'-yl-phosphate, monoanhydride with dichloromethylenebisphosphonic acid, trisodium salt The title salt was prepared according to the method of Example 1.

NMR δ³¹P (D₂O) 8.59 (d, J=18 Hz), 1.73 (dd, J=18 and 29 Hz), −9.94 (d, J=29 Hz).

EXAMPLE X

Quantification of $P_{2T}$-receptor agonist/antagonist activity in washed human platelets.

Preparation

Human venous blood (100 ml) was divided equally between 3 tubes, each containing 3.2% trisodium citrate (4 ml) as anti-coagulant. The tubes were centrifuged for 15 min at 240 G to obtain a platelet-rich plasma (PRP) to which 300 ng/ml prostacyclin (PGI₂, 3 µl/ml PRP of 1/10 diln. in saline from stock 1 mg/ml in ethanol) was added to stabilize the platelets during the washing procedure. Red cell free PRP was obtained by centrifugation for 10 min at 125 G followed by further centrifugation for 15 min at 640 G. The supernatant was discarded and the platelet pellet resuspended in modified, calcium free, Tyrode solution ((10 ml) CFT, composition: NaCl 137 mM (8 g/l), NaHCO₃ 11.9 mM (1 g/l), NaH₂PO₄ 0.38 mM (0.06 g/l), KCl 2.86 mM (1 ml of 20% soln./l), MgCl₂ 1.05 mM (1 ml of 10% soln./l), dextrose 5.55 mM (1 g/l)), gassed with 95% O₂/5% CO₂ and maintained at 37°. Following addition of a further 300 ng/ml PGI₂, the pooled suspension was centrifuged once more for 15 min at 640 G. The supernatant was discarded and the platelets resuspended initially in 10 ml CFT with further CFT added to adjust the final platelet count to 2×10⁵/µl. This final suspension was stored in a 60 ml syringe at 3° with air excluded.

To allow recovery from PGI₂-inhibition of normal function, platelets were used in aggregation studies no sooner than 2 hours after final resuspension. In all studies 430 µl aliquots of platelet suspension were added to siliconized aggregation cuvettes containing CaCl₂ solution (10 µl of 45 mM soln., final conc. 1 mM) and stirred at 900 rpm in a PAP4 aggregometer (Biodata). Human fibrinogen (Sigma, F 4883) and 8-sulphophenyltheophylline (8-SPT, to block any P₁ agonist activity of compounds) were added to give final concentrations of 0.2 mg/ml (10 µl of 10 mg/ml solution of clottable protein in saline) and 3×10⁻⁴M (10 µl of 5.6 mg/ml solution in 6% glucose), respectively. Recording of aggregation was then started.

Protocol a) Selection of submaximal ADP concentration

A concentration of ADP producing a just submaximal response was selected by constructing a concentration/response curve over the range 10–300 µM. The appropriate solution of ADP was added to the aggregation cuvette in a volume of 10 µl, 20 min after starting the aggregation trace. Aggregation responses were measured using the maximum rate of change in light transmission, an index given by the PAP4 slope-reader. The submaximal concentration of ADP selected at this stage of the protocol was used in the subsequent assessment of antagonist potency of the compounds. All measurements were made in duplicate in platelets from each donor.

b) Assessment of agonist/antagonist potency 5 min after starting the aggregation trace, saline or the appropriate solution of test compound was added to an aggregation cuvette in a volume of 30 µl to give a final concentration of 0, 10, 100 or 1000 µM. Aggregation at this point was indicative of agonist activity and, if it occurred, agonist potency was estimated by comparison with control ADP responses obtained in a). If aggregation did not occur the previously selected submaximal concentration of ADP was added in a volume of 10 μl, 15 min after the test compound. Antagonist potency was estimated as a % inhibition of the control ADP response to obtain an approximate $IC_{50}$. Compounds which completely inhibited the ADP response at the initial concentrations were retested at a lower concentration range. Compounds with an $IC_{50}<10^{-8}M$ were also retested in the absence of 8-SPT to confirm the lack of any $P_1$ agonist activity and with a 2 min rather than a 15 min incubation to check whether inhibition was time dependent.

Results

Results are reported as the negative logarithm of the antagonist potency ($pIC_{50}$) obtained in duplicate form from each of 4 donors. For compounds with $pIC_{50}>8$ a comment "clean" is made if there is no evidence of $P_1$ agonist activity. An $IC_{50}<3$ is defined as "inactive".

We claim:

1. A method of treating a patient to inhibit platelet aggregation, which method comprises the step of administering to a patient in need of such treatment a therapeutically effective amount of compound of formula I:

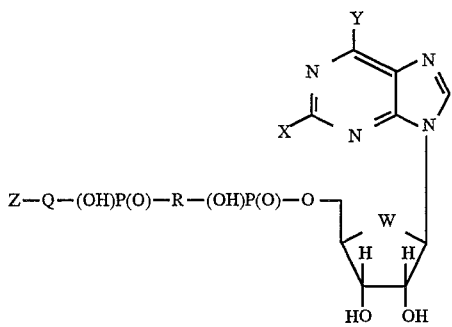

wherein

Q represents $CR^1R^2$

R represents O or $CR^3R^4$,

W represents O or $CH_2$ $R^1$, $R^2$, $R^3$ and $R^4$ independently represent hydrogen or halogen, X represents $SR^5$, $R^5$ represents ethyl, propyl, butyl or pentyl;

Y represents $NH_2$ or alkoxy $C_{1-6}$ and

Z represents an acidic moiety, in addition, when R represents $CR^3R^4$, then —Q—Z may also represent hydroxy or —OP(O)OH)$_2$;

or a pharmaceutically acceptable salt thereof.

2. A method of treating a patient to promote platelet disaggregation, which method comprises the step of administering to a patient in need of such treatment a therapeutically effective mount of compound of formula I:

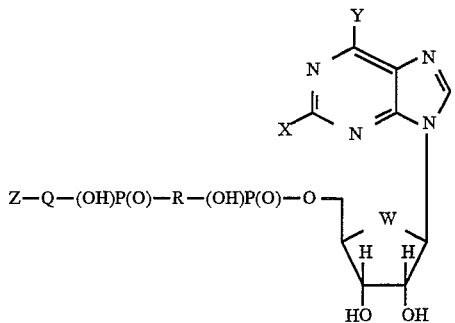

wherein

Q represents $CR^1R^2$

R represents O or $CR^3R^4$,

W represents O or $CH_2$ $R^1$, $R^2$, $R^3$ and $R^4$ independently represent hydrogen or halogen, X represents $SR^5$, $R^5$ represents ethyl, propyl, butyl or pentyl;

Y represents $NH_2$ or alkoxy $C_{1-6}$ and

Z represents an acidic moiety, in addition, when R represents $CR^3R^4$, then —Q—Z may also represent hydroxy or —P(O)OH)$_2$;

or a pharmaceutically acceptable salt thereof.

3. A compound of formula I,

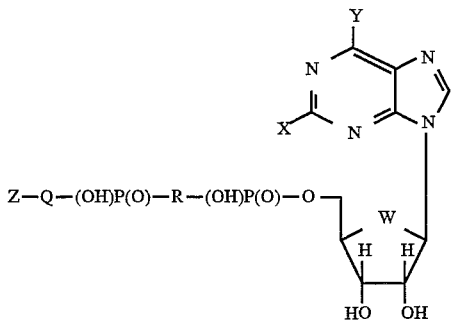

wherein

Q represents $CR^1R^2$

R represents O or $CR^3R^4$,

W represents O or $CH_2$ $R^1$, $R^2$, $R^3$ and $R^4$ independently represent hydrogen or halogen, X represents $SR^5$, $R^5$ represents ethyl, propyl, butyl or pentyl;

Y represents $NH_2$ or alkoxy $C_{1-6}$ and

Z represents an acidic moiety, in addition, when R represents $CR^3R^4$, then —Q—Z may also represent hydroxy or —OP(O)OH)$_2$;

and pharmaceutically acceptable salt thereof.

4. A compound of formula I, as defined in claim 3, or a pharmaceutically acceptable salt thereof, wherein Z is —P(O)(OH)$_2$.

5. A compound of formula I, as defined in claim 3, or a pharmaceutically acceptable salt thereof, wherein Q is $CR^1R^2$ and R is O.

6. A compound of formula 1, as defined in claim 3, or a pharmaceutically acceptable salt thereof, wherein W is O.

7. A compound of formula I, as defined in claim 3, which is

2-Propylthio-5'-adenylic acid, monoanhydride with dichloromethylenebisphosphonic acid, or a pharmaceutically acceptable salt thereof.

8. A compound of formula I, as defined in claim 3, which is

2-Propylthio-5'-adenylic acid, monoanhydride with dibromomethylenebisphosphonic acid, 2-Propylthio-5'-adenylic acid, monoanhydride with difluoromethylenebisphosphonic acid, 2-Pentylthio-5'-adenylic acid, monoanhydride with dichloromethylenebisphosphonic acid, 2-Pentylthio-5'-adenylic acid, monoanhydride with dibromomethylenebisphosphonic acid, 2-Ethylthio-5'-adenylic acid, monoanhydride with dichloromethylenebisphosphonic acid, 2-Ethylthio-5'-adenylic acid, monoanhydride with dibromomethylenebisphosphonic acid, 2-Butylthio-5'-adenylic acid, monoanhydride with dichloromethylenebisphosphonic acid, 2-Propylthio-5'-adenylic acid, monoanhydride with methylenebisphosphonic acid, 2-Propylthio-5'-adenylic acid, monoanhydride with sulphodifluoromethylphosphonic acid, 2-Propylthio-5'-adenylic acid, monoanhydride with phosphonoacetic acid, 2-(1-Methylethyl)thio-5'-adenylic acid, monoanhydride with dichloromethylenebisphosphonic acid, 2-Propylthioadenosine, 5'-$P^1$ monoester with bis[(dihydroxyphosphinyl) methyl]phosphinic acid, 2-Propylthioadenosine, 5'-$P^1$ monoester with bis[(dichloro(dihydroxyphosphinyl)methyl]phosphinic acid, 2-Propylthioadenosine, 5'-$P^1$ monoester with methylenebisphosphonic acid, $P^2$-monoanhydride with phosphoric acid, or 2-Propylthioadenosine 5'-$P^1$ monoester with methylenebisphosphonic acid, or a pharmaceutically acceptable salt of any one thereof.

9. A compound of formula I, as defined in claim 3, wherein Y is $NH_2$.

10. A pharmaceutical composition comprising a compound of formula I, as defined in claim 3, or a pharmaceutically acceptable salt thereof, in admixture with a pharmaceutically acceptable carrier, diluent or adjuvant.

11. A process for the preparation of a compound of formula I, as defined in claim 3 or a pharmaceutically acceptable salt thereof, which comprises a) producing a compound of formula I in which R represents O, or a salt thereof, by reacting a compound of formula II, or a salt thereof

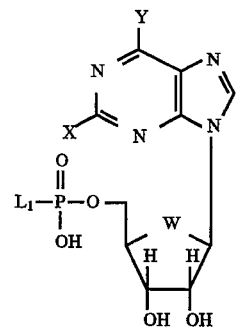

wherein W, X and Y are as defined in claim 3 and $L_1$ represents a leaving group, with a compound of formula III, or a salt thereof,

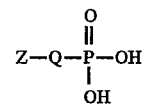

wherein Z and Q are as defined in claim 3;

b) producing a compound of formula I in which R represents $CR^3R^4$, or a salt thereof, by reacting a compound of formula IV, or a salt thereof,

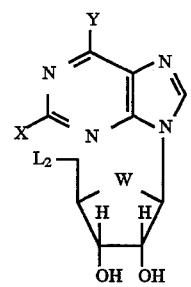

wherein W, X and Y are as defined in claim 3 and $L_2$ represents a leaving group, with a compound of formula V, or a salt thereof,

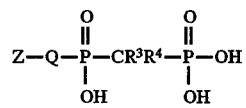

wherein Z, Q, $R^3$ and $R^4$ are as defined in claim 3;

c) producing a compound of formula I in which R is $CR^3R^4$ and —Q—Z is —OP(O)(OH)$_2$, or a salt thereof, by reacting a corresponding compound of formula I in which —Q—Z is hydroxy with a compound of formula VI, or a salt thereof,

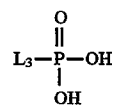

where $L_3$ is a leaving group;

d) removal of a protecting group from a corresponding protected compound of formula I in which one or more of the functional groups is protected, and where desired or necessary converting the resulting compound of formula I, or another salt thereof, to a pharmaceutically acceptable salt thereof or vice versa.

* * * * *